United States Patent
Yamane et al.

(10) Patent No.: US 11,585,795 B2
(45) Date of Patent: Feb. 21, 2023

(54) OPTICAL DETECTION TYPE CHEMICAL SENSOR

(71) Applicant: TIANMA JAPAN, LTD., Kanagawa (JP)

(72) Inventors: Haruki Yamane, Akita (JP); Kiyoshi Yamakawa, Akita (JP); Shingo Takahashi, Akita (JP); Koki Takahashi, Kanagawa (JP); Satoshi Miura, Kanagawa (JP); Koji Shigemura, Kanagawa (JP); Nobuya Seko, Kanagawa (JP); Ken Sumiyoshi, Kanagawa (JP)

(73) Assignee: TIANMA JAPAN, LTD., Kanagawa (JP)

( * ) Notice: Subject to any disclaimer, the term of this patent is extended or adjusted under 35 U.S.C. 154(b) by 53 days.

(21) Appl. No.: 17/392,736

(22) Filed: Aug. 3, 2021

(65) Prior Publication Data
US 2022/0042959 A1 Feb. 10, 2022

(30) Foreign Application Priority Data
Aug. 4, 2020 (JP) .............................. JP2020-132418

(51) Int. Cl.
*G01N 33/00* (2006.01)
*G01N 21/59* (2006.01)
*G01N 21/21* (2006.01)

(52) U.S. Cl.
CPC ....... *G01N 33/0027* (2013.01); *G01N 21/211* (2013.01); *G01N 21/59* (2013.01)

(58) Field of Classification Search
CPC .. G01N 33/0027; G01N 21/211; G01N 21/59; G01N 2021/218; G01N 2021/7779; G01N 21/77; G01N 21/17
See application file for complete search history.

(56) References Cited

U.S. PATENT DOCUMENTS 10,753,917 B2 * 8/2020 Tseng ..................... G01N 31/22
11,474,025 B2 * 10/2022 Seko ...................... G01N 21/21

FOREIGN PATENT DOCUMENTS

| JP | 3-067218 A | 3/1991 |
| JP | 2007-071866 A | 3/2007 |
| JP | 2007-120971 A | 5/2007 |
| JP | 2011-158307 A | 8/2011 |
| JP | 2017-172993 A | 9/2017 |

* cited by examiner

*Primary Examiner* — Seung C Sohn
(74) *Attorney, Agent, or Firm* — Sughrue Mion, PLLC

(57) ABSTRACT

An optical detection type chemical sensor includes a light source, a detection element and a photodetector. The detection element is constituted of a laminate in which a multilayer film including a chemical detection layer, an optical interference layer, and a half mirror layer is formed on a transparent substrate. At least one of the layers includes a magnetic material. Light from the light source is applied to the detection element under the condition that the light enters inside of the detection element from the rear surface of the transparent substrate on which the laminate is not formed and multiple reflection occurring in the laminate intensifies the magneto-optical effect. A subject is detected by using the photodetector to detect a magneto-optical signal indicating a change in reflected light from the laminate resulting from a change in an optical property resulting from a reaction in the chemical detection layer.

11 Claims, 16 Drawing Sheets

OPTICAL DETECTION TYPE CHEMICAL SENSOR

CROSS-REFERENCE TO RELATED APPLICATIONS

This non-provisional application claims priority under 35 U.S.C. § 119(a) on Patent Application No. 2020-132418 filed in Japan on Aug. 4, 2020, the entire content of which is hereby incorporated by reference.

BACKGROUND

This disclosure relates to a chemical sensor that detects a chemical substance, and specifically, relates to an optical detection type chemical sensor that relies on the magneto-optical effect in a laminate including a chemical detection layer, a half mirror layer, and an optical interference layer formed on a transparent substrate.

In recent years, chemical sensors that detect the type of chemical substance and the concentration thereof have been in development. In various areas such as fuel cells and hydrogen vehicles, for example, hydrogen gas has garnered attention as a next generation energy source, and in such areas, hydrogen gas sensors that detect hydrogen are being developed as chemical sensors. Hydrogen gas disperses readily, is susceptible to leaking, and has a very high risk of exploding if a leak were to occur. In order to use hydrogen safely, a hydrogen gas sensor that combines a high degree of reliability with a high degree of convenience that allows for installation in various locations is indispensable.

Depending on the detection method, various types of sensors such as a contact combustion type, a semiconductor type, a gas thermal conduction type, an electrochemical type, and an optical type have been proposed as hydrogen gas sensors that detect hydrogen gas leaks.

The first three types are commercially widely available. Contact combustion type sensors detect hydrogen gas by detecting heat generated by catalytic combustion through contact with hydrogen as a change in resistance in a Pt line coil. This sensor has excellent quantitativity due to the ability thereof to attain an output proportional to the gas concentration, and is suited to detecting leakage of high concentration hydrogen gas. Semiconductor type sensors detect hydrogen gas through changes in electrical resistance resulting from a hydrogen reduction reaction at the surface of an oxide semiconductor such as $SnO_2$, and is suited to detecting low concentrations of hydrogen gas. Gas thermal conduction type sensors rely on the difference in thermal conductivity between the relevant gas and a standard gas (typically air). Such sensors rely on the property of hydrogen gas of having a thermal conductivity much higher than other flammable gases, and are used in detecting high concentrations of hydrogen. The response time of these sensors typically ranges from one second to dozens of seconds.

Such hydrogen gas sensors that are entering common use typically require high operating temperatures for improved response speed, the cleaning effect, and the like, with operations at 200° C. or greater being typical. Also, every type of sensor captures the response of the elements in the form of an electrical signal, and thus, excessive current or sparks in an electric circuit in contact with the hydrogen gas pose the risk of ignition.

Optical detection type hydrogen gas sensors that detect hydrogen gas leakage through an optical method have been proposed as sensors that avoid the risk of explosions resulting from the electrical circuit.

In one proposed technique, light is applied to a detection catalyst that undergoes a change in light absorption upon contact with hydrogen gas, and hydrogen gas is detected by receiving the light that has passed through or been reflected by the detection catalyst. In another proposed technique, a laser beam is emitted, and the resulting Raman-scattered light produced by hydrogen gas is detected. In these hydrogen gas sensors, changes in the intensity of transmitted light, reflected light, or Raman-scattered light are detected as detection signals. Thus, a fluctuation in the output from the light source or dust entering the optical path of the measurement light could cause a fluctuation in the detection signal, resulting in erroneous operation. Optical detection type hydrogen gas sensors that detect hydrogen gas leakage through the magneto-optical effect have been proposed as optical detection type hydrogen gas sensors that can avoid the issue of erroneous operation due to fluctuation in the output of the light source and the effect of dust.

The hydrogen gas sensor has a detection element constituted of a thin film laminate including a hydrogen gas detection layer, a magnetic layer, an optical interference layer, and a reflective layer. Light is emitted under the condition that the light enters the inside of the detection element from the surface of the detection element in which the hydrogen gas detection layer is formed and the magneto-optical effect (e.g., change in polarizing angle) of incident light intensifies resulting from multiple reflection occurring in the laminate, and a magneto-optical signal that is reflected light from the detection element is measured to detect hydrogen gas. When the hydrogen gas detection layer comes into contact with hydrogen gas, the state of multiple reflection occurring in the laminate changes, causing the magneto-optical signal to greatly change, enabling detection of hydrogen gas at a high sensitivity. The magneto-optical signal (e.g., change in polarizing angle) is not affected by fluctuations in intensity of the measurement light, and thus, with this type of sensor, it is possible to detect in a stable manner the leakage of hydrogen gas without erroneous operation even if there are fluctuations in output from the light source.

SUMMARY

An aspect of the present disclosure is an optical detection type chemical sensor, including: a light source; a detection element; and a photodetector. The detection element is constituted of a laminate in which a multilayer film including a chemical detection layer, an optical interference layer, and a half mirror layer is formed on a transparent substrate. At least one of the chemical detection layer, the optical interference layer, and the half mirror layer constituting the laminate includes a magnetic material. When light emitted from the light source is applied to the detection element, the light is emitted from the light source under the condition that the light enters the inside of the detection element from the rear surface of the transparent substrate on which the laminate is not formed and multiple reflection occurring in the laminate intensifies the magneto-optical effect. A subject to be detected is detected by using the photodetector to detect a magneto-optical signal indicating a change in reflected light from the laminate resulting from a change in an optical property resulting from a reaction in the chemical detection layer.

It is to be understood that both the foregoing general description and the following detailed description are exemplary and explanatory and are not restrictive of this disclosure.

DETAILED DESCRIPTION OF EMBODIMENTS

In an optical detection type chemical sensor of this disclosure, a detection element that detects a subject to be detected is constituted of a laminate that includes a chemical detection layer, a half mirror layer, and an optical interference layer that are formed on a transparent substrate, and any one of the chemical detection layer, the optical interference layer, and the half mirror layer contains a magnetic material. The subject is detected by applying light onto the detection element so that the light enters the inside of the detection element from the rear surface of the transparent substrate on which the laminate is not formed, relying on the effect that the magneto-optical signal is intensified by multiple reflection at the laminate. Examples of subjects to be detected by the optical detection type chemical sensor include pH; gases such as hydrogen, oxygen, carbon dioxide, chlorine, and nitrogen oxide; DNA and enzymes; and the like, and the optical detection type chemical sensor is an optical detection type ion sensor that detects pH, an optical detection type gas sensor that detects a gas, or an optical detection type biosensor that detects DNA and enzymes, for example. In the embodiments below, an optical detection type hydrogen gas sensor that detects hydrogen gas will be described in detail as one such example.

Embodiments of this disclosure will be described below with reference to the drawings.

Embodiment 1

Figure 1:
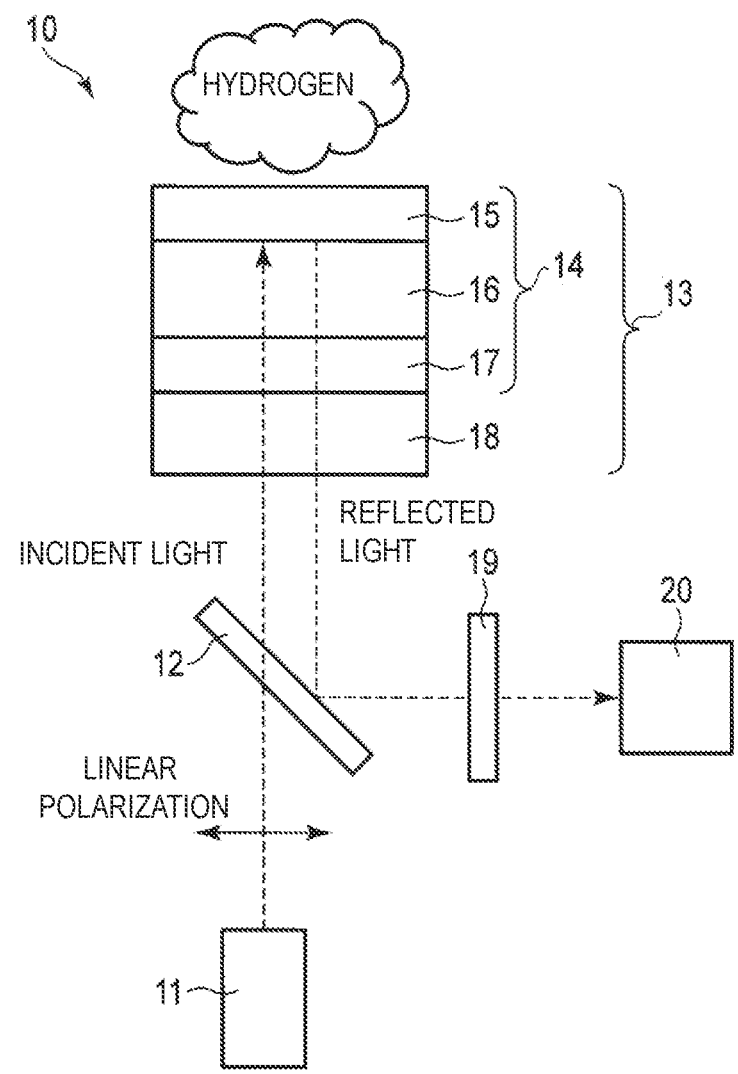
FIG. 1 is a configuration drawing that schematically shows an optical detection type hydrogen gas sensor of Embodiment 1.
Figure 2:
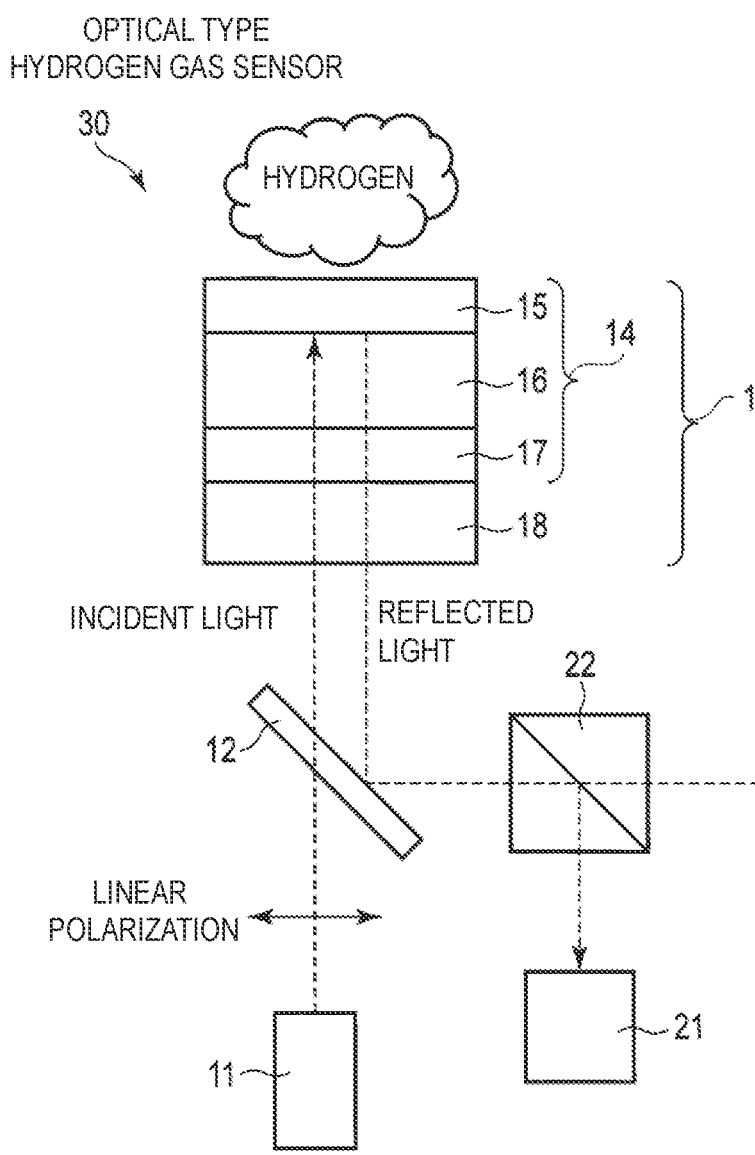
FIG. 2 is a configuration drawing that schematically shows another optical detection type hydrogen gas sensor of Embodiment 1.

FIGS. 1 and 2 are configuration drawings that schematically show optical detection type hydrogen gas sensors 10 and 30 of Embodiment 1 of this disclosure. The broken line arrows in the drawings are optical paths, the optical detection type hydrogen gas sensors 10 and 30 are based on a perpendicular incidence optical system, and hydrogen gas is detected by applying light to the rear surface of a transparent substrate 18 on which a laminate 14 that actually detects hydrogen gas not is formed, the light being emitted from the normal direction in relation to the transparent substrate 18. In the present embodiment, the optical detection type hydrogen gas sensors 10 and 30 are constituted of a light source 11 for applying linearly polarized light onto the laminate 14 formed on the transparent substrate 18, an optical splitter 12 that guides the light emitted from the laminate 14 via the transparent substrate 18 to a photodetector 20 or photodetectors 20 and 21, a polarizer 19 or a polarizing optical splitter 22 for detecting changes in the polarizing angle of reflected light due to the magneto-optical effect in the laminate 14, and the photodetector 20 or the photodetectors 20 and 21 for detecting a change in intensity in the light that has passed through the polarizer 19 or the polarizing optical splitter 22.

It is preferable that the light source 11, which emits linearly polarized light, be a monochromatic light source that emits light at a single wavelength such as a semiconductor laser or a gas laser, and in particular, that a polarizer such as a Glan-Thompson prism be used in order to improve linear polarization properties.

As shown in FIGS. 1 and 2, the detection element 13 is constituted of a laminate 14 in which a half mirror layer 17, an optical interference layer 16, and a hydrogen gas detection layer 15 are layered in the stated order on the transparent substrate 18, and detects hydrogen gas by measuring a magneto-optical signal that indicates a change in the polarizing angle of reflected light resulting from a change in optical properties such as the refractive index or the absorption coefficient of the hydrogen gas detection layer 15 resulting from contact with hydrogen gas. Here, at least one of the half mirror layer 17, the optical interference layer 16, and the hydrogen gas detection layer 15 constituting the laminate 14 contains a magnetic material. Also, the optical interference layer 16 needs to have a thickness sufficient to cause light applied to the laminate 14 to undergo multiple reflection within the laminate 14, and specifically, it is preferable that a value resulting from multiplying the thicknesses and refractive indices of the half mirror layer 17 and the optical interference layer 16 and adding together the resulting products be greater than approximately ¼ the wavelength of the emitted light. Additionally, the half mirror layer 17 needs to have a thickness enabling the light applied to the laminate 14 to enter the interior of the laminate 14, and specifically, it is preferable that the thickness of the half mirror layer 17 be 30 nm or less. Also, the hydrogen gas detection layer 15 needs to have a thickness sufficient to reflect the light that has entered the interior of the laminate 14, and specifically, it is preferable that the thickness of the hydrogen gas detection layer 15 be 20 nm or greater.

The material used for the hydrogen gas detection layer 15 can be any material as long as the material undergoes a change in optical properties such as the refractive index and the absorption coefficient upon reacting with hydrogen gas, but in particular, it is preferable that a thin film having Pd (palladium), which undergoes a great change in optical properties through contact with hydrogen gas, as the primary component be used. Furthermore, in this case, Pd has the property of occluding and discharging hydrogen gas at room temperature, and thus, exhibits the effect of allowing for a hydrogen gas sensor that can be operated at room temperature, and that has a high detection sensitivity.

Examples of materials to use for the optical interference layer 16 include typical transparent oxides, transparent nitrides, or transparent fluorides such as $SiO_2$ (silicon dioxide), ZnO (zinc oxide), MgO (magnesium oxide), $TiO_2$ (titanium oxide), MN (aluminum nitride), $MgF_2$ (magnesium fluoride), and it is preferable that the material have a high transmittance for wavelengths of light emitted from the light source 11. Examples of materials to use for the half mirror layer 17 include typical metal materials made of metals such as Ag (silver), Al (aluminum), Au (gold), and Cu (copper) or alloys of such metals, and it is preferable that the material have a high reflectance for wavelengths of light emitted from the light source 11.

Examples of the magnetic material contained in at least one of the hydrogen gas detection layer 15, the optical interference layer 16, and the half mirror layer 17 constituting the laminate 14 include typical magnetic materials including metals such as Fe (iron), Co (cobalt), and Ni (nickel) or alloys thereof, or oxides such as ferrite that include Fe as the primary component, but in particular, it is preferable that the magnetic material be a perpendicular magnetization film such as a CoPt (cobalt/platinum) alloy film, an FePt (iron/platinum) alloy film, a Co/Pd (cobalt/palladium) multilayer film, or a Co/Pt (cobalt/platinum) multilayer film. In this case, the magneto-optical signal can be greatly intensified due to multiple reflection occurring in the laminate, and thus, the material exhibits the advantageous effect of being able to detect hydrogen gas at a high sensitivity.

Next, the principles by which hydrogen gas is detected by the optical detection type hydrogen gas sensors 10 and 30 of the present embodiment will be described with reference to FIGS. 3A to 3D.

Here, a case is considered in which, when linearly polarized light with a wavelength of AO is applied to the laminate 14 constituting the detection element 13, the light undergoes multiple reflection within the laminate 14, resulting in the greatest change in the polarizing angle of light emitted from the laminate 14.

Figure 3A:
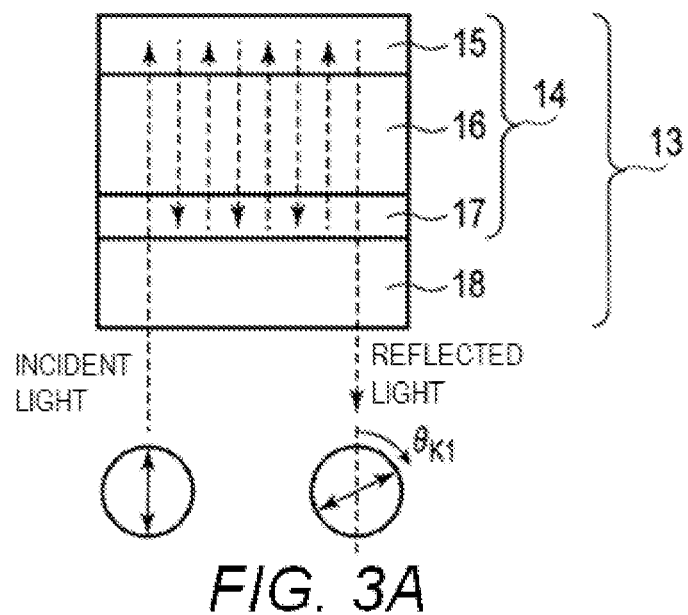
FIGS. 3A to 3D are descriptive drawings showing the magneto-optical properties of a detection element of the optical detection type hydrogen gas sensor shown in FIGS. 1 and 2, and the principle by which hydrogen gas is detected.
Figure 3B:
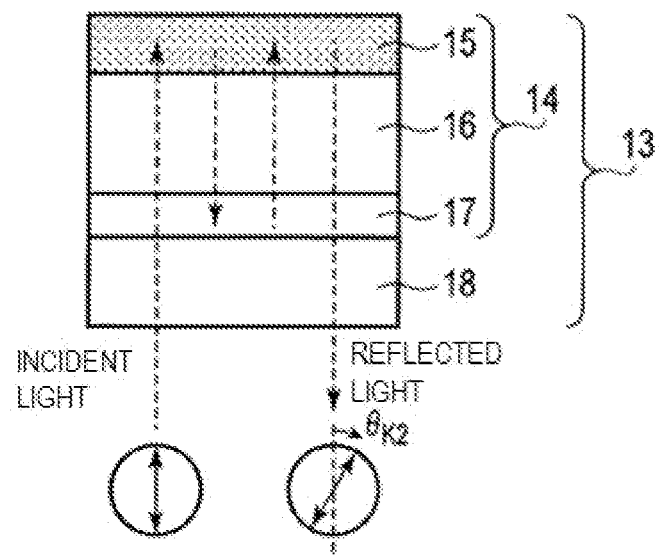
Figure 3C:
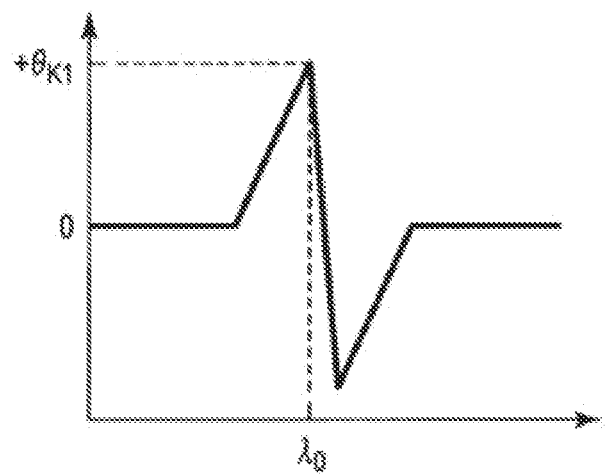
Figure 3D:
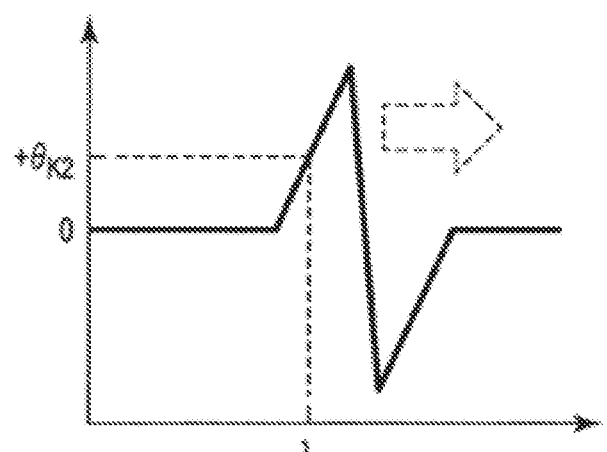

In a laminate 14 configured in this manner, if linearly polarized light were emitted in a state where magnetization of the contained magnetic material is saturated in one direction, then as shown in FIG. 3A, the emitted light is subjected to a heavy magneto-optical effect due to multiple reflection within the laminate 14, resulting in the light being emitted with a large polarizing angle ($+\theta K1$). At this time, as shown in FIG. 3C, the laminate 14 has a magneto-optical resonance spectrum in which the sign of the magneto-optical effect inverts abruptly at a specific wavelength of measurement light (resonant wavelength). Next, if in this state, the hydrogen gas detection layer 15 comes into contact with hydrogen gas, then as shown in FIG. 3B, the optical properties such as the refractive index or the absorption coefficient of the hydrogen gas detection layer change, resulting in a change in the optical interference state of light in the laminate 14. That is, with the introduction of hydrogen gas, the magneto-optical resonance spectrum shifts to the longer wavelength region (rightward direction in the diagram) as shown in FIGS. 3C and 3D, for example. At this time, the effect of multiple reflection is reduced, resulting in the polarizing angle of the emitted light ($+\theta K2$) becoming less than in an initial state without hydrogen gas ($\theta K1 > \theta K2$).

The magnitude of shift in the magneto-optical resonance spectrum depends on the concentration of hydrogen gas. Thus, by measuring the magneto-optical signal indicating the polarizing angle of the light reflected by the laminate 14, it is possible to detect the concentration of the hydrogen gas.

Specifically, as shown in FIG. 1, the light emitted from the laminate 14 is guided by the optical splitter 12 towards the photodetector 20. At this time, by arranging the polarizer 19 set at a prescribed detection angle in front of the photodetector 20, the intensity of the light passing through the polarizer 19 differs according to the polarizing angle of the light emitted from the laminate 14, and thus, it is possible to measure the magneto-optical signal indicating the change in the polarizing angle as a change in intensity of the light, and thus, it is possible for the photodetector 20 to detect the presence or absence of hydrogen gas on the basis of the measurement results.

Furthermore, the use of the differential detection method is effective as a method for improving measurement accuracy for the magneto-optical signal as shown in FIG. 2. In this case, a polarizing beam splitter 22 is used instead of the polarizer 19. By passing through the polarizing beam splitter 22, the reflected light from the laminate 14 is split into two beams of light: p-polarized light and s-polarized light. The two beams of light are respectively detected by two photodetectors 20 and 21, and the change in polarizing angle is measured by taking the difference in intensity between the beams of light detected by the photodetectors 20 and 21. According to this method, even if dust were to enter the optical path or the intensity of light emitted from the light source 11 were to fluctuate, it is possible to measure the magneto-optical signal with low noise and to detect the concentration of the hydrogen gas at a high accuracy.

In the optical detection type hydrogen gas sensors 10 and 30 described above, by performing synchronous detection or Fourier analysis by periodically changing the intensity of light emitted from the light source 11 to the laminate 14 so as to periodically change the magneto-optical signals detected by the photodetector 20 or the photodetectors 20 and 21, it is possible to improve detection sensitivity by reducing noise in the magneto-optical signal.

In the present embodiment, a case was described in which hydrogen gas is detected by measuring the reduction in the polarizing angle, but the configuration is not limited thereto. The conditions for increasing the polarizing angle as a result of the hydrogen gas detection layer 15 coming into contact with hydrogen gas can be set by using light sources of differing wavelengths or changing the thickness and material of each layer of the laminate 14.

Working Example 1

Figure 4A:
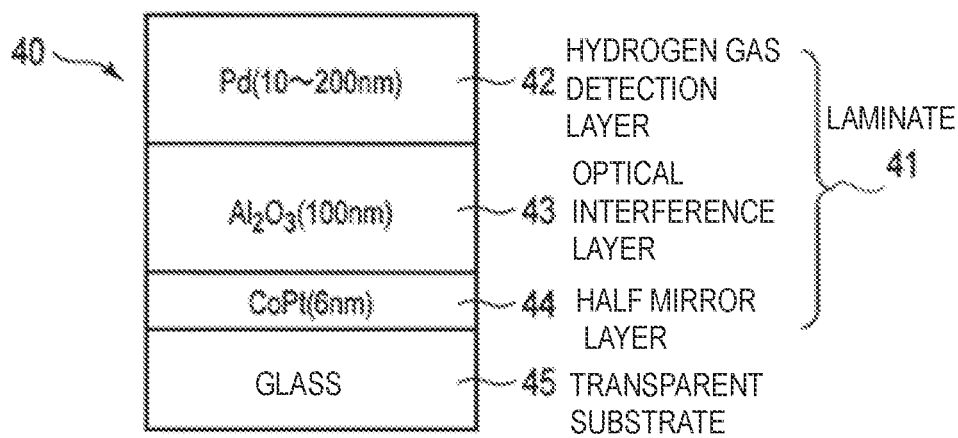
FIGS. 4A to 4C include a cross-sectional view that schematically shows the detection element of the optical detection type hydrogen gas sensor of Working Example 1 and characteristic diagrams thereof.
Figure 4B:
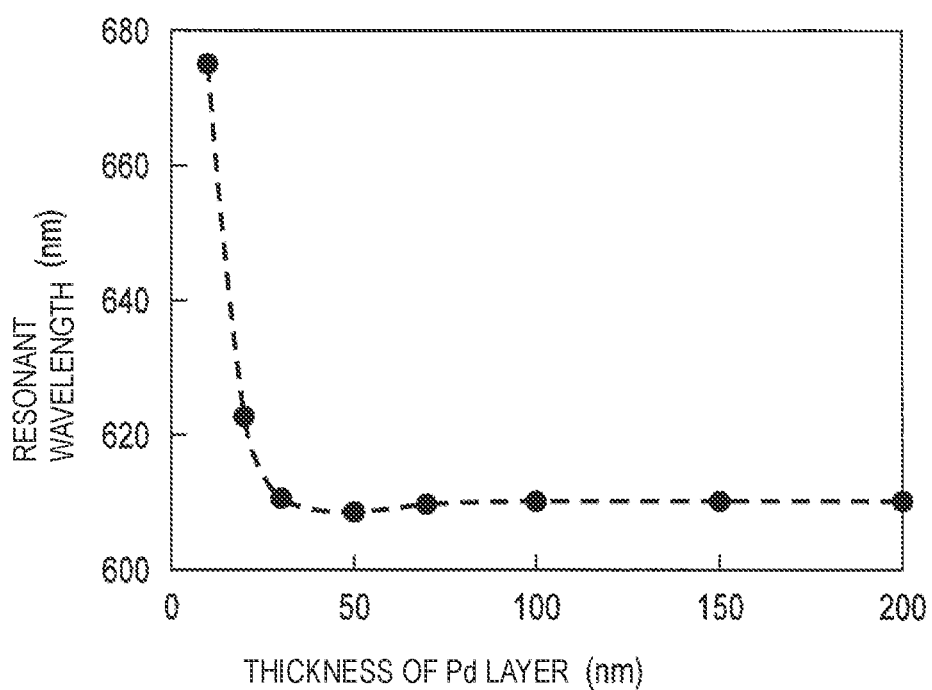
Figure 4C:
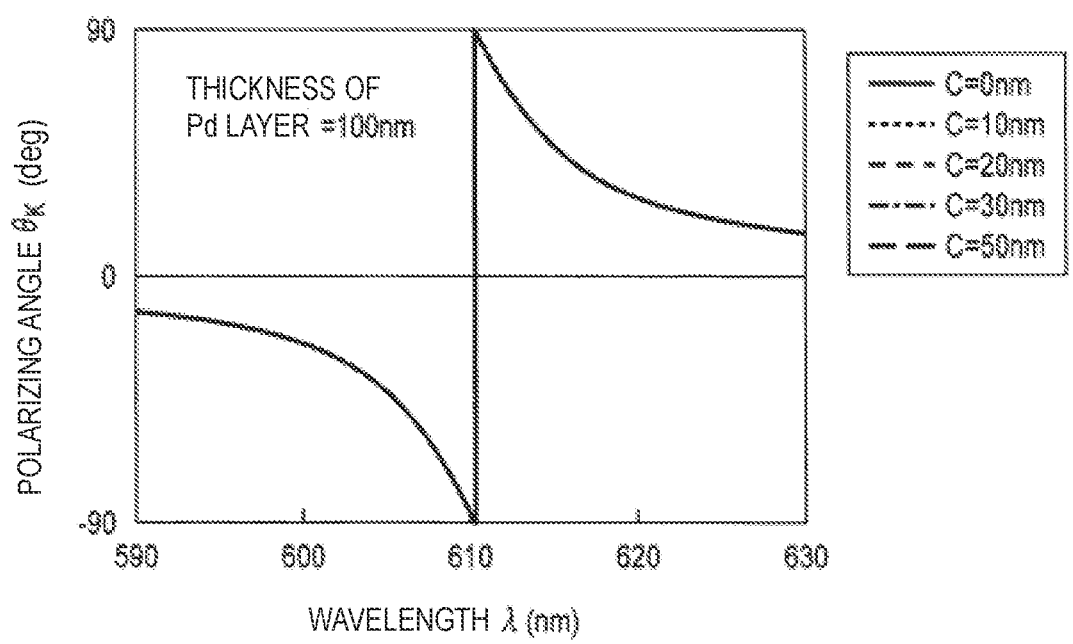

FIGS. 4A to 4C include a cross-sectional view that schematically shows the detection element 40 of the optical detection type hydrogen gas sensor of Working Example 1 of the present embodiment, and characteristic diagrams from a computer simulation.

The detection element 40 of the present working example is, as shown in FIG. 4A, constituted of a laminate 41 in which a half mirror layer 44, an optical interference layer 43, and a hydrogen gas detection layer 42 are formed on a transparent substrate 45. Specifically, the laminate 41 is constituted of a structure in which a CoPt alloy thin film that is a magnetic material with a thickness of 6 nm as the half mirror layer 44, an $Al_2O_3$ (aluminum oxide) thin film with a thickness of 100 nm as the optical interference layer 43, and a Pd (palladium) thin film with a thickness of 10-200 nm as the hydrogen gas detection layer 42 are layered in the stated order on a glass substrate.

FIGS. 4B and 4C show the results of a computer simulation indicating the properties of the laminate 41 for a case in which light is applied to the detection element 40 so that the light enters the inside of the detection element from the rear surface of the transparent substrate 45 on which the laminate 41 is not formed. FIG. 4B shows the change in the resonant wavelength in which the sign of the magneto-optical effect inverts, within the magneto-optical resonance spectrum shown in FIGS. 3A to 3D, for when the thickness of the Pd thin film that detects the hydrogen gas is changed. FIG. 4B is a characteristic diagram indicating the effect of the surface state of the hydrogen gas detection layer 42, and as the thickness of the Pd layer increases to 20 nm and beyond, no great fluctuation is seen in the resonant wavelength. That is, by setting the thickness of the hydrogen gas detection layer 42 to 20 nm or greater, it is possible to reduce fluctuations resulting from the surface state of the hydrogen gas detection layer 42, and it is possible to detect hydrogen gas in a stable manner. As an example, FIG. 4C shows the effect on magneto-optical properties of forming a carbon thin film (C) on the surface of the Pd layer having a thickness of 100 nm in the detection element 40 having the Pd layer. That is, in this computer simulation, a carbon thin film is formed as simulated contamination on the surface of the detection element 40. Cases in which the carbon thin film has a thickness of 0 nm, 10 nm, 20 nm, 30 nm, and 50 nm are shown, but the simulation results are the same for all five cases with no difference being seen in the magneto-optical resonance spectrum, and thus, it can be inferred that this detection element 40 is not greatly affected by surface contamination.

Figure 5A:
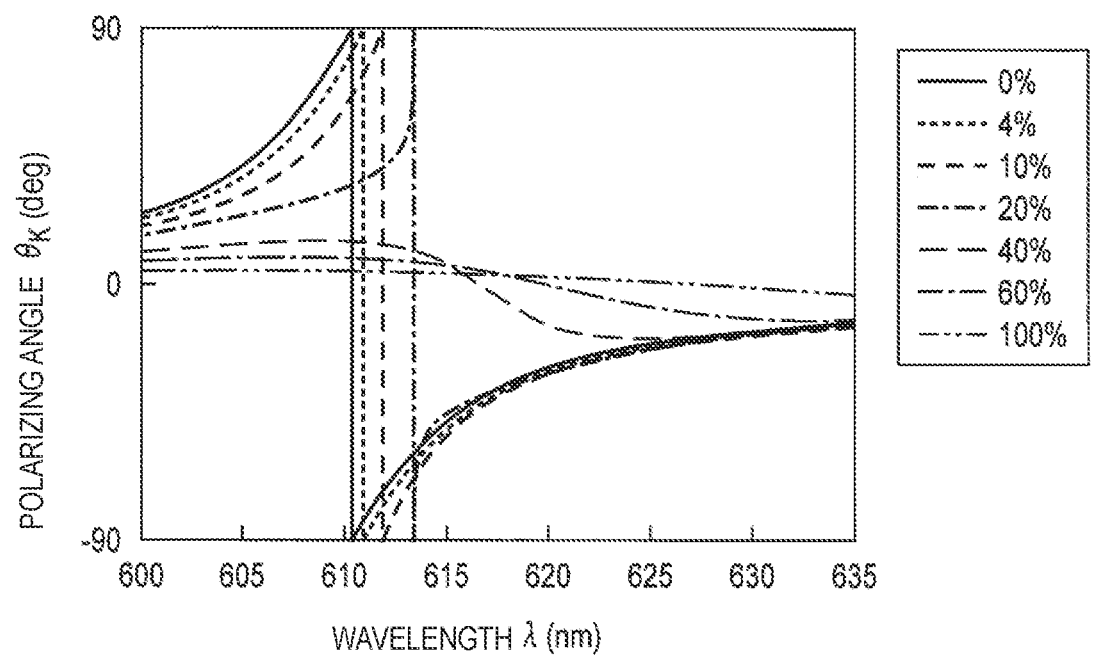
FIGS. 5A and 5B are characteristic diagrams indicating a computer simulation of detection of hydrogen gas by the detection element shown in FIGS. 4A to 4C.
Figure 5B:
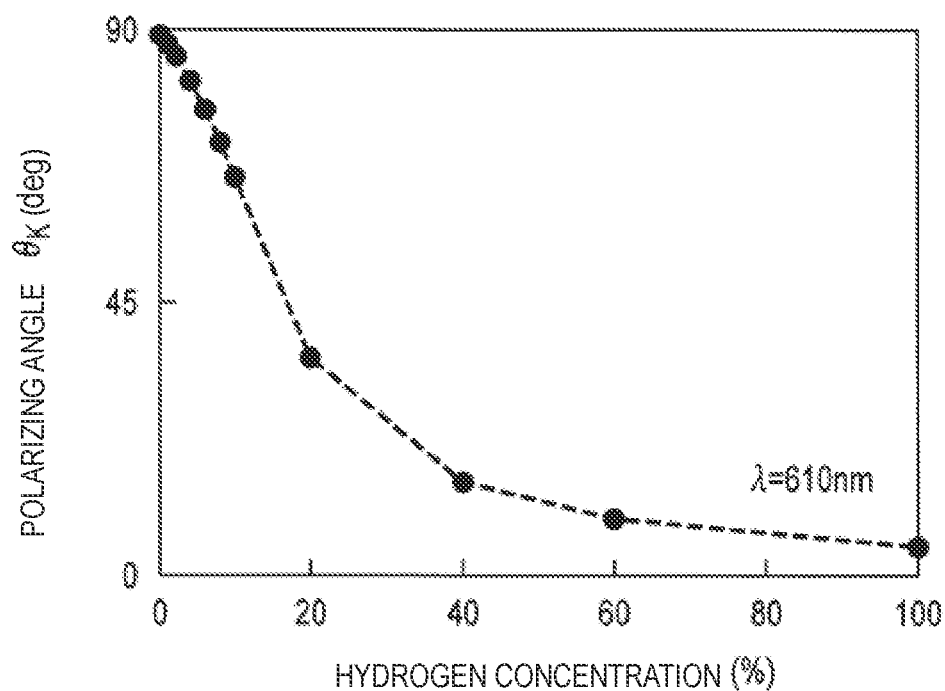

FIGS. 5A and 5B are characteristic diagrams indicating a computer simulation of detection of hydrogen gas by the detection element 40 having the Pd layer with a thickness of 100 nm. Pd is known for its property that the optical properties thereof (refractive index and absorption coefficient) change as a result of hydrogen gas occlusion. Thus, when the detection element 40 comes into contact with hydrogen gas, the optical properties of the Pd layer formed on the surface of the detection element 40 change, and as described with reference to FIGS. 3A to 3D, the magneto-optical resonance spectrum shifts to the longer wavelength region (rightward direction in FIGS. 5A and 5B). FIG. 5A shows the change in magneto-optical resonance spectrum of the laminate 41 as the concentration of the hydrogen gas occluded in the Pd layer changes among 0%, 4%, 10%, 20%, 40%, 60%, and 100%. The degree of shift in the magneto-optical resonance spectrum changes according to the hydrogen concentration, and thus, as shown in FIG. 5B, the polarizing angle of the light (with a wavelength of 610 nm, for example) reflected from the laminate 41 decreases as the hydrogen concentration increases. By measuring the magneto-optical signal indicating the change in polarizing angle of the light reflected by the detection element 40 using the method described with reference to FIG. 1 or 2, it is possible to detect the concentration of the hydrogen gas.

In the present working example, a case was described in which the half mirror layer 44 of the laminate 41 is a CoPT alloy thin film that is a magnetic material, but the configuration is not limited thereto. As long as at least one of the hydrogen gas detection layer 42, the optical interference layer 43, or the half mirror layer 44 contains a magnetic material such as if the half mirror layer 44 is constituted of a multilayer film including a non-magnetic metal thin film and a magnetic thin film or magnetic microparticles are embedded in the optical interference layer 43, hydrogen gas can be detected by a similar method.

Embodiment 2

Figure 6:
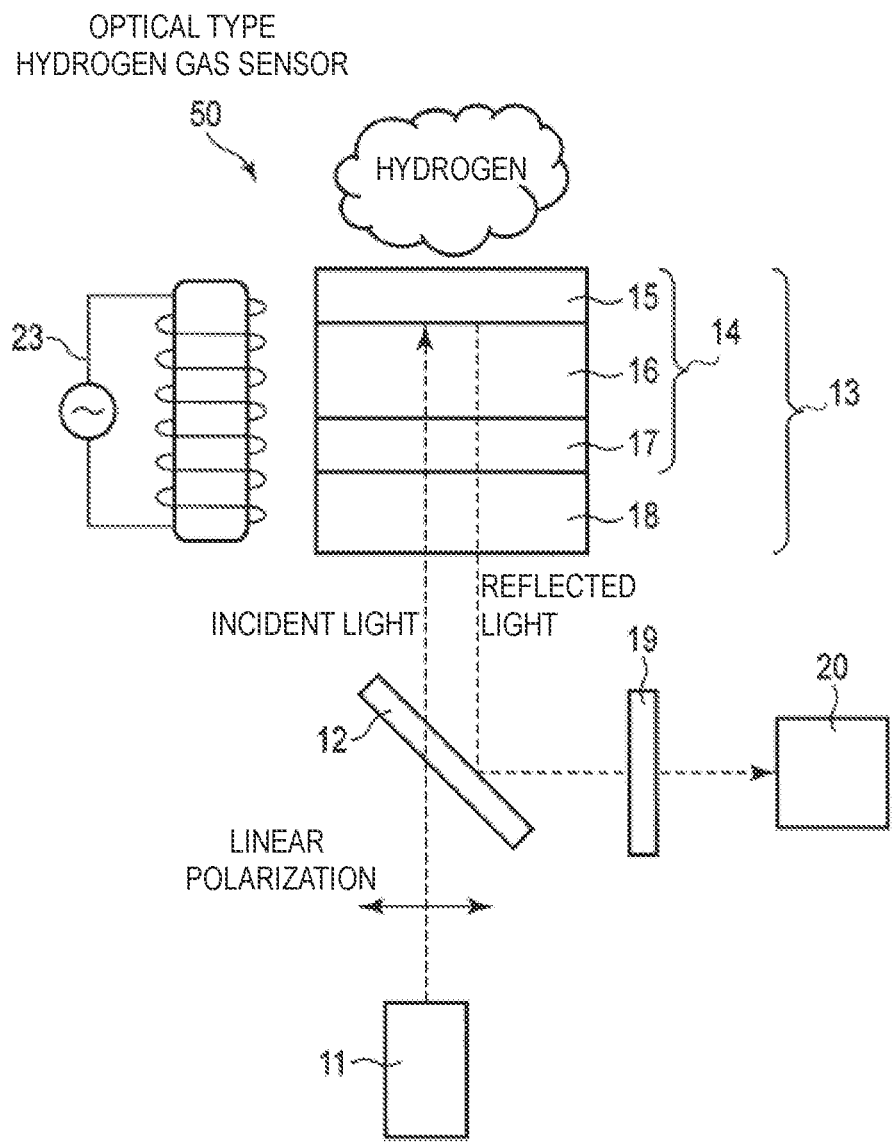
FIG. 6 is a configuration drawing that schematically shows an optical detection type hydrogen gas sensor of Embodiment 2.

FIG. 6 is a configuration drawing that schematically shows an optical detection type hydrogen gas sensor 50 of Embodiment 2 of this disclosure. Similar to Embodiment 1, the broken line arrows in the drawing are optical paths, the optical detection type hydrogen gas sensor 50 is based on a perpendicular incidence optical system, and hydrogen gas is detected by applying light to the rear surface of a transparent substrate 18 on which a laminate 14 that actually detects hydrogen gas is formed, the light being emitted from the normal direction in relation to the transparent substrate 18. In the present embodiment, the optical detection type hydrogen gas sensor 50 is constituted of a light source 11 for applying linearly polarized light onto the laminate 14, an optical splitter 12 that guides the light reflected by the laminate 14 via the transparent substrate 18 to a photodetector 20, a polarizer 19 for measuring changes in the polarizing angle of the reflected light due to the magneto-optical effect in the laminate 14, the photodetector 20 for detecting a change in intensity in the light that has passed through the polarizer 19, and a magnetic field application mechanism 23. Therefore, the optical detection type hydrogen gas sensor 50 of the present embodiment is similar to that of Embodiment 1 shown in FIG. 1 other than including the magnetic field application mechanism 23.

Similar to Embodiment 1, the detection element 13 of the optical detection type hydrogen gas sensor 50 of the present embodiment is constituted of a laminate 14 formed on the transparent substrate 18 by layering a half mirror layer 17, an optical interference layer 16, and a hydrogen gas detection layer 15 in the stated order, and additionally, at least one of the half mirror layer 17, the optical interference layer 16, and the hydrogen gas detection layer 15 contains a magnetic material. It is preferable that the structure of the laminate 14 and the material and thickness of each layer constituting the laminate 14 be similar to those of Embodiment 1 for similar reasons to Embodiment 1.

Similar to Embodiment 1, the optical detection type hydrogen gas sensor 50 of the present embodiment detects hydrogen gas by detecting the change in optical properties of the hydrogen gas detection layer 15 resulting from contact with hydrogen gas as a magneto-optical signal that indicates the change in the light emitted from the laminate 14. The present embodiment differs from Embodiment 1 in that the magneto-optical signal detected by the photodetector 20 is modulated by periodically changing the magnetization direction of the magnetic material contained in the laminate 14 using the magnetic field generated by the magnetic field application mechanism 23.

Next, the principles by which hydrogen gas is detected by the optical detection type hydrogen gas sensor 50 of the present embodiment will be described with reference to FIGS. 7A to 7D.

Here, a case is considered in which, when linearly polarized light is applied to the laminate 14 constituting the detection element 13, the light undergoes multiple reflection within the laminate 14, resulting in the polarizing angle of the reflected light reaching a maximum.

Figure 7A:
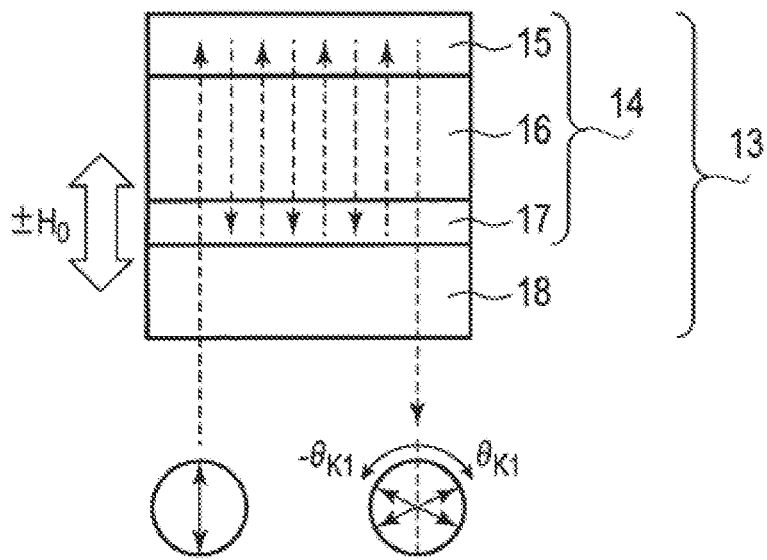
FIGS. 7A to 7D are descriptive drawings showing the magneto-optical properties of a detection element of the optical detection type hydrogen gas sensor shown in FIG. 6, and the principle by which hydrogen gas is detected.
Figure 7B:
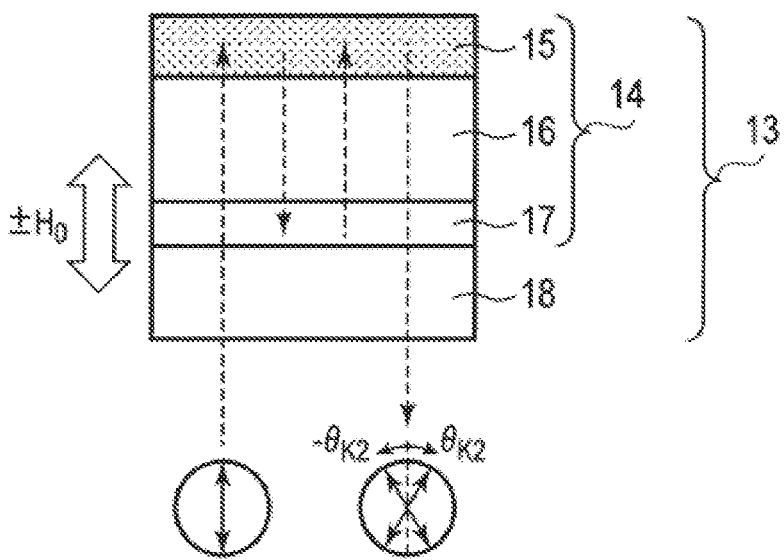
Figure 7C:
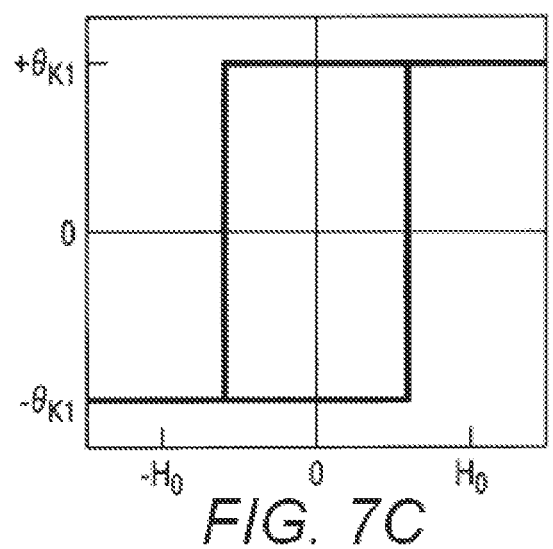
Figure 7D:
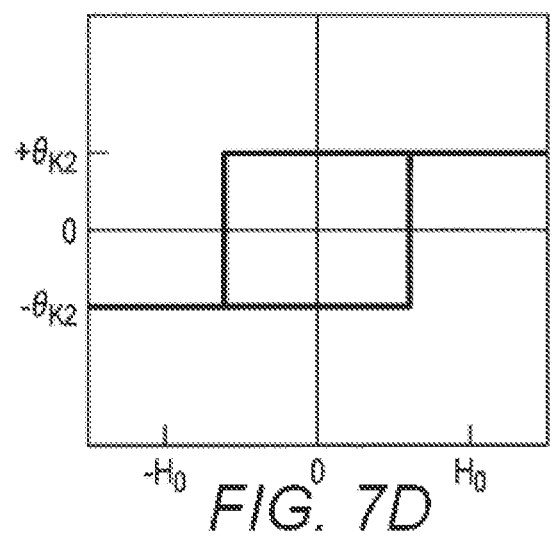

In a laminate 14 configured in this manner, if linearly polarized light were emitted in a state where the magnetic field application mechanism 23 applies a magnetic field (+HO or −HO) having a prescribed intensity allowing for magnetization of the contained magnetic material to occur in one direction, then as shown in FIG. 7A, the emitted light is subjected to a heavy magneto-optical effect due to multiple reflection within the laminate 14. As a result, the light is emitted at a large polarizing angle with differing signs (+θK1 or −θK1) depending on the direction of the applied magnetic field. Next, as shown in FIG. 7B, if the hydrogen gas detection layer 15 comes into contact with hydrogen gas in a state where the magnetic field (+HO or −HO) is applied, then the optical properties such as the refractive index or the absorption coefficient of the hydrogen gas detection layer change, resulting in a change in the optical interference conditions of light in the laminate 14. The effect of multiple reflection is reduced, resulting in the polarizing angle of the emitted light (|θK2|) becoming less than in an initial state without hydrogen gas (|θK1|>|θK2|). The polarizing angle of the light emitted from the laminate 14 differs depending on the direction of magnetization of the magnetic material contained in the laminate 14 and the presence or absence of hydrogen gas, and thus, the magneto-optical curves for when the direction and intensity of the magnetic field applied to the laminate 14 are changed are as shown in FIGS. 7C and 7D.

Thus, by detecting the magneto-optical signal indicating the change in polarizing angle of the light emitted by the laminate 14 while the magnetic field application mechanism 23 applies a magnetic field (±HO) that changes periodically to the laminate 14 at a prescribed intensity, it is possible to detect the presence or absence of hydrogen gas. Specifically, the light emitted from the laminate 14 is guided by the optical splitter 12 shown in FIG. 6 towards the photodetector 20. At this time, by arranging the polarizer 19 set at a prescribed detection angle in front of the photodetector 20, the intensity of the light passing through the polarizer 19 differs according to the polarizing angle of the light emitted from the laminate 14, and thus, it is possible to measure, using the photodetector 20, the magneto-optical signal indicating the change in the polarizing angle as a change in intensity of the light.

Additionally, at this time, the magneto-optical signal detected by the photodetector 20 is detected in synchronization with the magnetic field applied by the magnetic field application mechanism 23 to the laminate 14. Thus, using a magnetic field that changes periodically by passing an AC current through a coil to perform synchronous detection or Fourier analysis is effective for improving detection sensitivity by reducing noise in the magneto-optical signal.

In the optical detection type hydrogen gas sensor 50 described above, the use of the differential detection method is effective as a method for further improving detection accuracy as described in Embodiment 1 with reference to FIG. 2. In this case, a polarizing beam splitter is used instead of the polarizer 19. By passing through the polarizing beam splitter, the light emitted by the laminate 14 is split into two beams of light: p-polarized light and s-polarized light. The two beams of light are respectively detected by two photodetectors, and the magneto-optical signal is measured by taking the difference in intensity between the beams of light detected by the photodetectors. In this method, it is possible in particular to perform detection with low noise despite fluctuations in intensity of the light emitted from the light source 11, and it is possible to further increase detection accuracy for hydrogen gas.

Working Example 2

Figure 8:
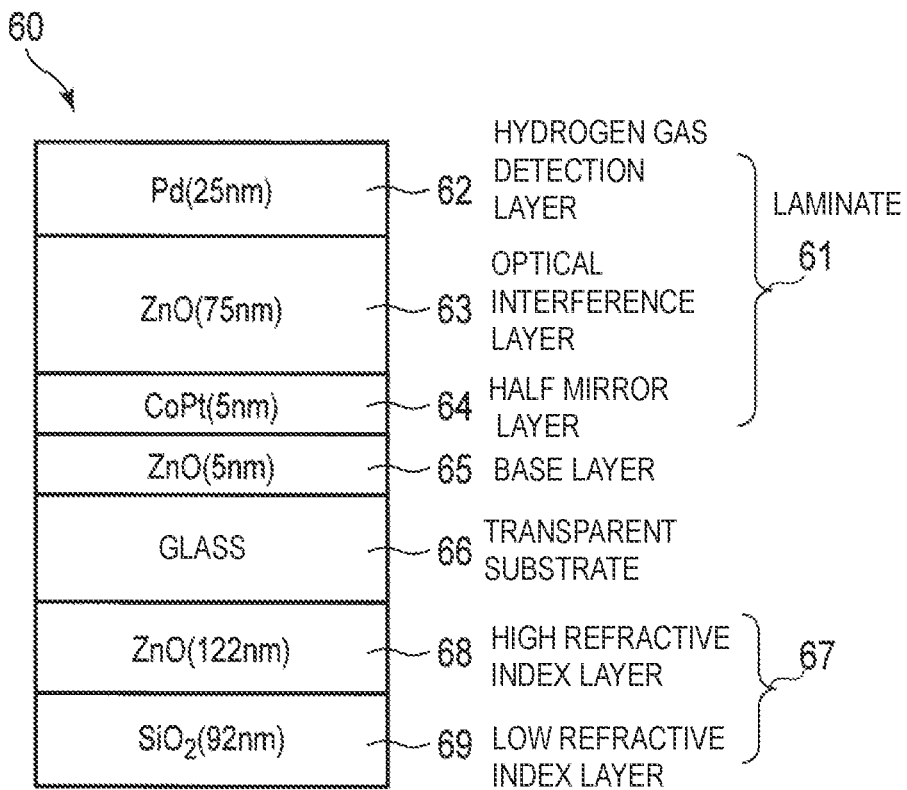
FIG. 8 is a cross-sectional view that schematically shows the detection element of the optical detection type hydrogen gas sensor of Working Example 2.

FIG. 8 is a cross-sectional view that schematically shows a detection element 60 of an optical detection type hydrogen gas sensor 50 of Working Example 2 of the present embodiment.

The detection element 60 of the present working example is formed by forming a base layer 65 made of a ZnO thin film with a thickness of 5 nm on a transparent substrate 66 and forming thereon a laminate 61 that actually detects hydrogen gas. The laminate 61 is constituted of a structure in which a CoPt alloy thin film that is a magnetic material with a thickness of 5 nm as a half mirror layer 64, a ZnO thin film with a thickness of 75 nm as an optical interference layer 63, and a Pd thin film with a thickness of 25 nm as a hydrogen gas detection layer 62 are layered in the stated order on the transparent substrate 66, which is a glass substrate. Additionally, an anti-reflection film 67 is formed on the rear surface of the transparent substrate 66 on which the laminate 61 is not formed in order to reduce the amount of light reflected by the transparent substrate 66. The anti-reflection film 67 is constituted of a structure in which a ZnO thin film with a thickness of 122 nm as a high refractive index layer 68, and an SiO$_2$ thin film with a thickness of 92 nm as a low refractive index layer are layered in the stated order on the glass substrate.

Figure 9A:
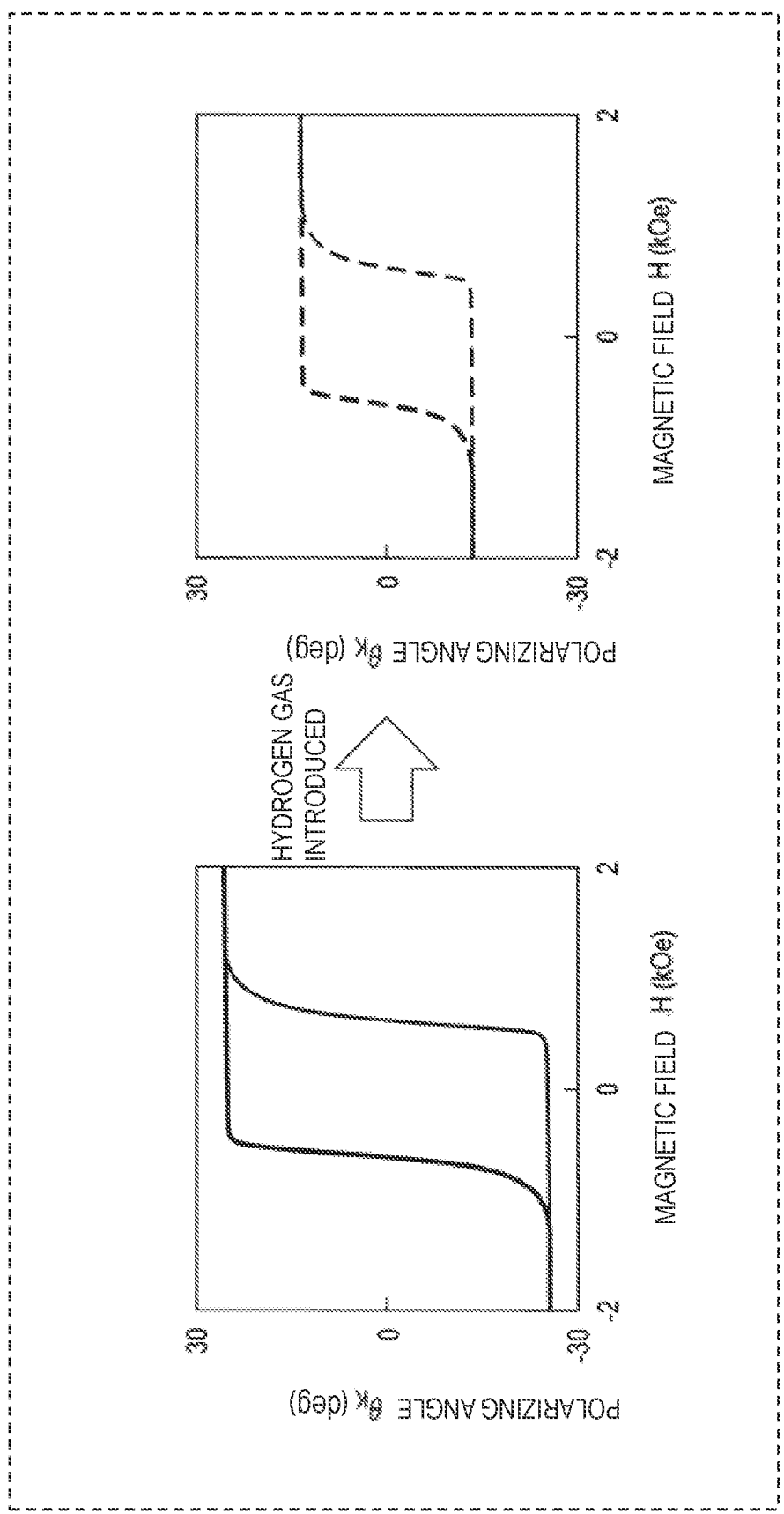
FIGS. 9A and 9B are characteristic diagrams indicating detection of hydrogen gas by the detection element shown in FIG. 8.
Figure 9B:
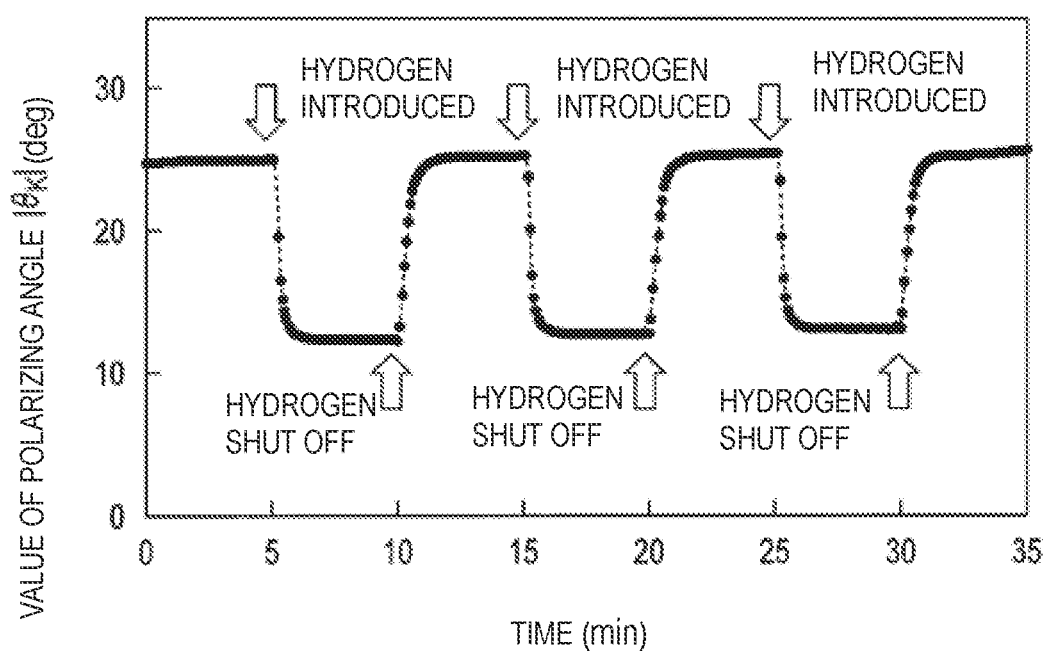

FIGS. 9A and 9B are results from an experiment in which a mixed gas of nitrogen and 4% hydrogen was actually detected by this detection element 60. A semiconductor laser with a wavelength of 658 nm was used as the light source 11 for measuring the magneto-optical signal, and light that was linearly polarized by passing through a polarizer was applied to the rear surface of the glass substrate on which the anti-reflection film 67 was formed, onto the detection element 60 from the normal direction of the glass substrate. FIG. 9A is a characteristic diagram of the magneto-optical effect of the detection element 60 for when the applied magnetic field was changed from −2.0 kOe (downward direction in FIGS. 7A to 7D) to +2.0 kOe (upward direction in FIGS. 7A to 7D) in a nitrogen gas atmosphere for the left hand diagram and a 4% hydrogen mixed gas atmosphere for the right hand diagram. The polarizing angle of the reflected light from the detection element 60 changes as the direction of magnetization of the CoPt magnetic metal layer of the laminate 61 changes. As the detection element 60 comes into contact with hydrogen gas, the optical properties of the Pd that is the hydrogen gas detection layer 62 change, causing the multiple reflection state of the laminate 61 to change, resulting in the amount of change in polarizing angle of the light emitted from the detection element 60 being reduced.

Additionally, FIG. 9B shows the change over time in the size of the polarizing angle of light emitted from the detection element 60 when pure nitrogen gas and a mixed gas of nitrogen and 4% hydrogen are alternately introduced in a state where pulse magnetic fields with intensities of −1.5 kOe and +1.5 kOe are alternately applied to the detection element. As can be understood from FIG. 9A as well, the magnetization direction of the CoPT alloy thin film of the laminate is upward or downward depending on the sign of the applied magnetic field. In FIG. 9B, the magneto-optical signal as hydrogen gas is introduced or shut off can be observed, and it can be confirmed that the detection element 60 is actually functioning as a hydrogen gas sensor.

Embodiment 3

Figure 10:
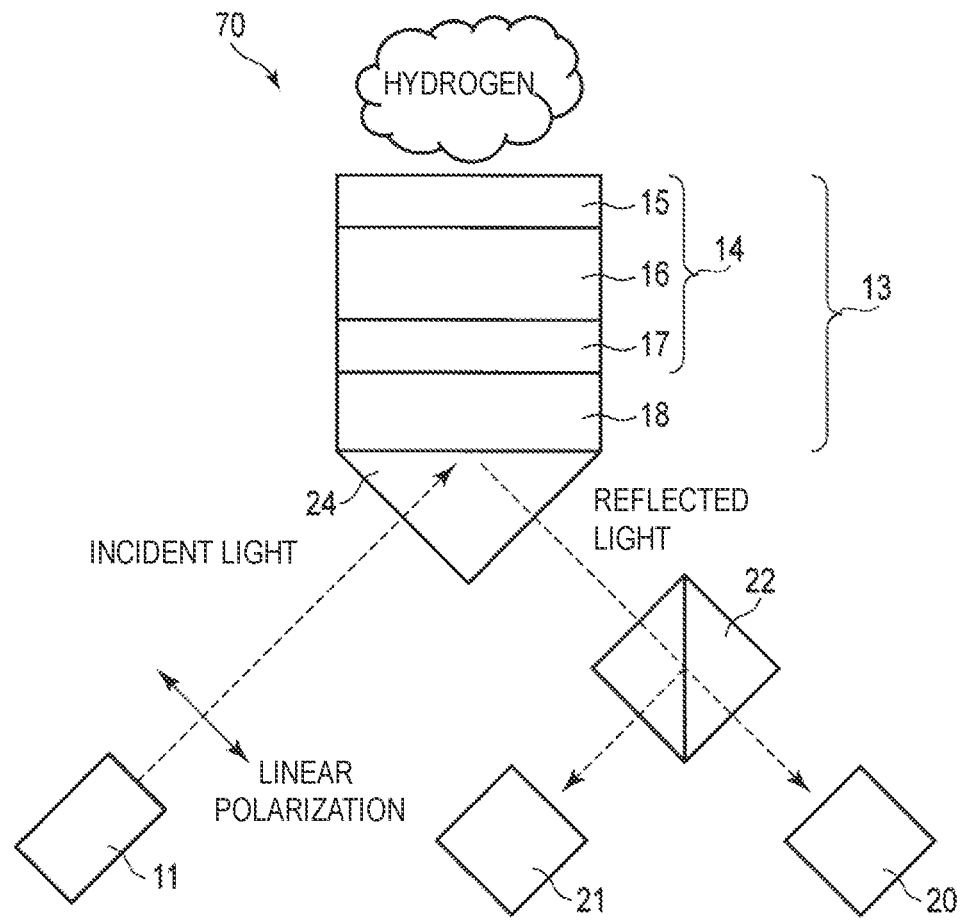
FIG. 10 is a configuration drawing that schematically shows an optical detection type hydrogen gas sensor of Embodiment 3.

FIG. 10 is a configuration drawing that schematically shows an optical detection type hydrogen gas sensor 70 of Embodiment 3 of this disclosure. The broken lines in the drawing are optical paths, the optical detection type hydrogen gas sensor 70 is based on a diagonal incidence optical system, and hydrogen gas is detected by applying light to the rear surface of a transparent substrate 18 on which a laminate 14 that actually detects hydrogen gas is not formed, the light being emitted from the diagonal direction via a prism 24. In the present embodiment, the optical detection type hydrogen gas sensor 70 is constituted of a light source 11 for applying linearly polarized light from the diagonal direction onto the detection element 13 via the prism 24, a polarizing beam splitter 22 for measuring the change in polarizing angle of the light emitted from the detection element 13, and a photodetectors 20 and 21 for detecting a change in the intensity of light that has passed through the polarizing beam splitter 22. Therefore, the optical detection type hydrogen gas sensor 70 of the present embodiment is similar to that of Embodiment 1 shown in FIG. 2 other than light being applied to the detection element 13 in the diagonal direction using the prism 24.

Similar to Embodiments 1 and 2, the detection element 13 of the optical detection type hydrogen gas sensor 70 of the present embodiment is constituted of a laminate 14 formed on the transparent substrate 18 by layering a half mirror layer 17, an optical interference layer 16, and a hydrogen gas detection layer 15 in the stated order, and additionally, at least one of the half mirror layer 17, the optical interference layer 16, and the hydrogen gas detection layer 15 contains a magnetic material. It is preferable that the structure of the laminate 14 and the material and thickness of each layer constituting the laminate 14 be similar to those of Embodiments 1 and 2 for similar reasons to Embodiments 1 and 2.

Similar to Embodiment 1 described with reference to FIGS. 3A to 3D, the optical detection type hydrogen gas sensor 70 of the present embodiment detects hydrogen gas by detecting the change in optical properties of the hydrogen gas detection layer 15 resulting from contact with hydrogen gas as a magneto-optical signal that indicates the change in the light emitted from the detection element. Specifically, the reflected light from the laminate 14 that has passed through the prism 24 is split by the polarizing beam splitter 22 into two beams of light: p-polarized light and s-polarized light. The two beams of light are respectively detected by two photodetectors 20 and 21, and the change in polarizing angle is measured by taking the difference in intensity between the beams of light detected by the photodetectors 20 and 21.

In the optical detection type hydrogen gas sensor 70 described above, using a coil or the like to change the direction of magnetization of the magnetic material contained in the laminate 14 to modulate the magneto-optical signal is effective as a method for further improving detection accuracy as described in Embodiment 2. Also, periodically changing the intensity of light emitted from the light source 11 to the laminate 14 to modulate the magneto-optical signals detected by the photodetectors 20 and 21 is effective, and performing synchronous detection or Fourier analysis is effective for further improving detection sensitivity by reducing noise in the magneto-optical signal, similar to Embodiments 1 and 2.

Working Example 3

Figure 11:
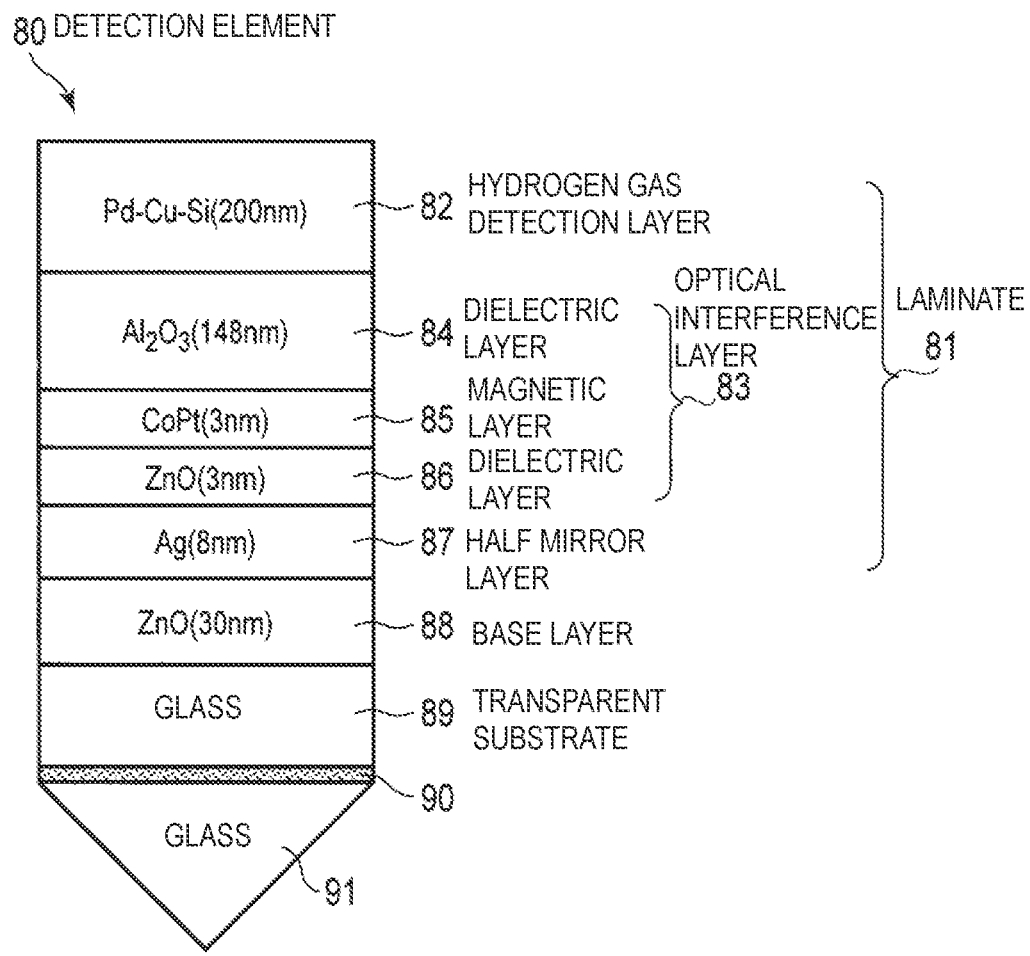
FIG. 11 is a cross-sectional view that schematically shows the detection element of the optical detection type hydrogen gas sensor of Working Example 3.

FIG. 11 is a cross-sectional view that schematically shows a detection element 80 of an optical detection type hydrogen gas sensor 70 of Working Example 3 of the present embodiment.

The detection element 80 of the present working example is formed by forming a base layer 88 made of a ZnO thin film with a thickness of 30 nm on a transparent substrate 89 and forming thereon a laminate 81 that actually detects hydrogen gas. The laminate 81 is constituted of a structure in which an Ag thin film with a thickness of 8 nm as a half mirror layer 87, a $ZnO/CoPt/Al_2O_3$ multilayer thin film as an optical interference layer 83, and a Pd—Cu—Si alloy thin film with a thickness of 200 nm as a hydrogen gas detection layer 82 are layered in the stated order on the transparent substrate 89, which is a glass substrate. The optical interference layer 83 constituted of a multilayer film in which a CoPt thin film with a thickness of 3 nm that is a magnetic layer 85 is interposed between a ZnO thin film with a thickness of 3 nm that is a dielectric layer 86 and an $Al_2O_3$ thin film with a thickness of 148 nm that is another dielectric layer 84. That is, in the present working example, the optical interference layer 83 of the laminate 81 contains a magnetic material. Also, a prism 91 is optically coupled, using an optical coupling oil 90, to the rear surface of the transparent substrate 89 on which the laminate 81 is not formed in order to reduce the amount of light reflected by the transparent substrate 89. The optical coupling oil 90 reduces the reflection of light at the boundary between the transparent substrate 89 and the prism 91.

Figure 12A:
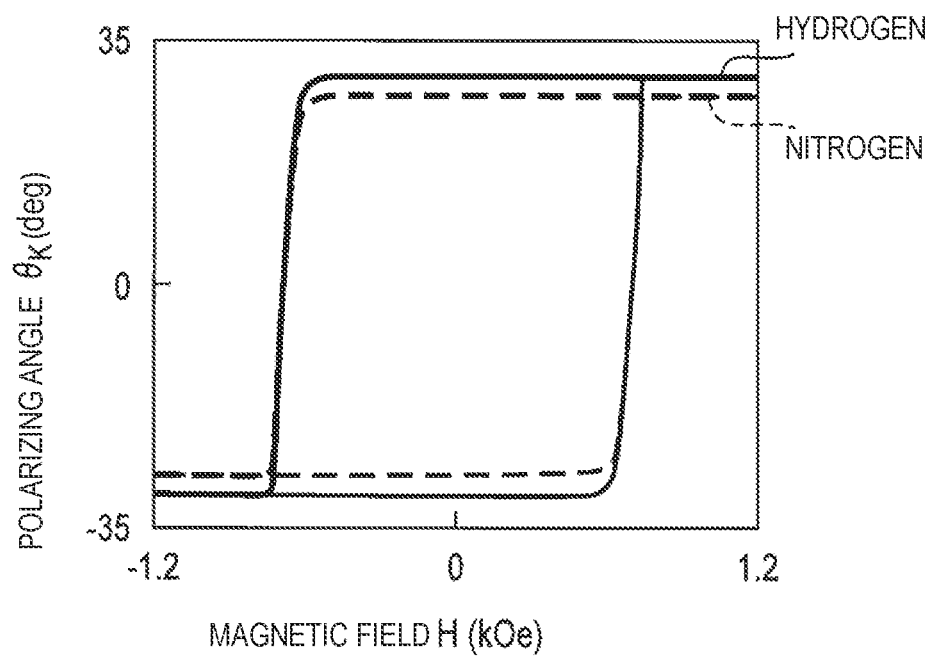
FIGS. 12A and 12B are characteristic diagrams indicating detection of hydrogen gas by the detection element shown in FIG. 11.
Figure 12B:
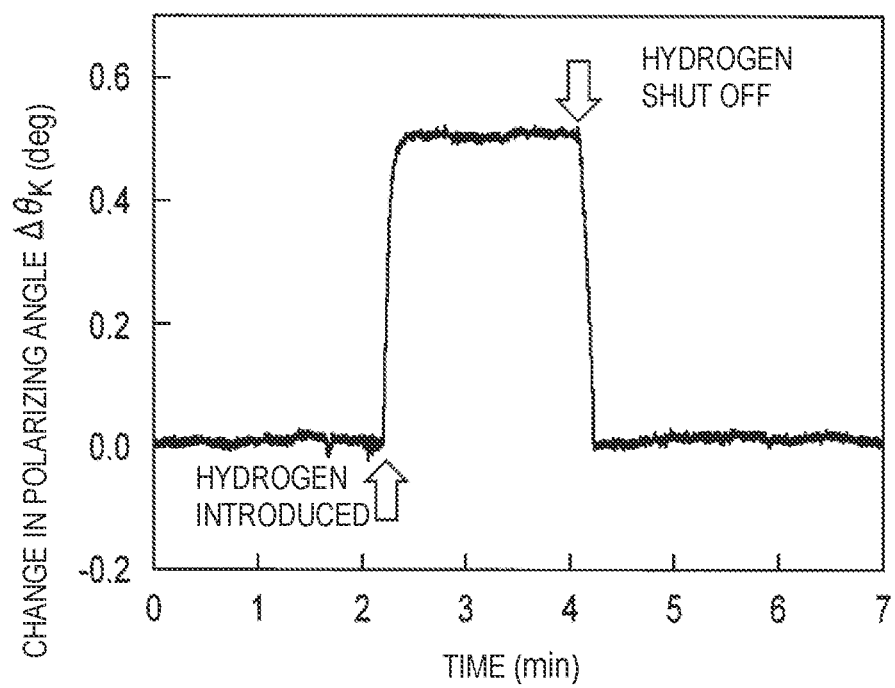

FIGS. 12A and 12B are results from an experiment in which a mixed gas of nitrogen and 4% hydrogen was actually detected by the detection element 80. A semiconductor laser with a wavelength of 658 nm was used as the light source 11 for measuring the magneto-optical signal, and light that was linearly polarized by passing through a polarizer was applied to the rear surface of the glass substrate via the prism 91 onto the detection element 80 at an angle of 45 degrees to the normal direction. FIG. 12A is a characteristic diagram of the magneto-optical effect of the detection element 80 for when the applied magnetic field was changed from −1.2 kOe (downward direction in FIG. 11) to +1.2 kOe (upward direction in FIG. 11) in a nitrogen gas atmosphere and a 4% hydrogen mixed gas atmosphere. As the hydrogen gas detection layer 82 comes into contact with hydrogen gas, the multiple reflection condition of the laminate 81 changes, resulting in an increase in the amount of change in polarizing angle of the light emitted from the detection element 80.

Additionally, FIG. 12B shows the change in size of the polarizing angle of reflected light when the atmosphere is changed from a pure nitrogen gas atmosphere to a mixed gas atmosphere of nitrogen and 4% hydrogen in a state where no magnetic field is applied to the detection element 80. The magneto-optical signal as hydrogen gas is introduced or shut off can be observed, and it can be confirmed that the detection element 80 is actually functioning as a hydrogen gas sensor.

In the present working example, a case was described in which hydrogen gas is detected by measuring the increase in the polarizing angle, but the configuration is not limited thereto. Similar to Working Example 1 or 2, the conditions for decreasing the polarizing angle as a result of the hydrogen gas detection layer 83 coming into contact with hydrogen gas can be set by using light sources of differing wavelengths or adjusting the thickness or changing the material of each layer of the laminate 81.

This disclosure was described above on the basis of Embodiments 1, 2, and 3 and working examples, but the present disclosure is not limited thereto. In the description above, the direction of the magnetic field applied to the laminate using the magnetic field application mechanism is the direction perpendicular to the surface of the laminate containing the magnetic material, but the configuration is not limited thereto. As long as conditions are set such that light applied to the laminate causes an increase in intensity of the magneto-optical signal due to multiple reflection, the direction in which the magnetic field is applied maybe the horizontal direction in relation to the surface of the laminate; in this case, it is preferable that the magnetic material contained in the laminate be Fe, Co, Ni, or an alloy thereof, such materials having an axis of easy magnetization in the in-plane direction. Additionally, in the present disclosure, a change in polarizing angle occurring when linearly polarized light is applied to a magnetic material was used for the magneto-optical signal, but the configuration is not limited thereto. It is also possible to use another type of magneto-optical signal such as that resulting from a change in intensity of the reflected light or a change in ellipticity occurring when linearly or circularly polarized light is applied to a magnetic material. Also, this disclosure describes the use of a glass substrate as the transparent substrate, but the configuration is not limited thereto. As long as the substrate is transparent to light used for measurement, another material can be used for the substrate, and if using an infrared light source, for example, a semiconductor substrate that uses a material such as Si or GaAs can be used. Additionally, an optical fiber reflection probe constituted of a plurality of optical probes can be used as a method for applying light from the light source to the detection element and guiding the reflected light from the detection element to the photodetectors. In this case, a configuration can be adopted in which detection elements are formed directly on the tips of the optical probes.

In embodiments above, an optical detection type hydrogen gas sensor was given as an example of the optical detection type chemical sensor, but the optical detection type chemical sensor of this disclosure is not limited to being the optical detection type hydrogen gas sensor, and the optical detection type chemical sensor can be applied to an optical detection type ion sensor that detects pH, an optical detection type gas sensor that detects a gas, or an optical detection type biosensor that detects DNA and enzymes, for example. Thus, similar effects to the above embodiments can be exhibited when the optical detection type chemical sensor is applied to an optical detection type ion sensor that detects pH, an optical detection type gas sensor that detects a gas, or an optical detection type biosensor that detects DNA and enzymes, for example.

The optical detection type chemical sensor of this disclosure can be used as a gas sensor that detects leakage or measures the concentration of gases such as hydrogen, oxygen, carbon dioxide, chlorine, and nitrogen oxide; an ion sensor that detects pH; and a biosensor that detects DNA, enzymes, and the like.

As described above, this disclosure provides a highly reliable optical detection type chemical sensor that can stably detect a subject to be detected with a simple device configuration.

In the case of conventional optical detection type hydrogen gas sensors, the thickness of the hydrogen gas detection layer formed on the surface of the detection element is very thin, at a few nm, and the optical properties of the detection element are very sensitive to the surface state of the detection element, resulting in the detection performance changing over time. Thus, improvement is sought in terms of long-term reliability. Additionally, in order to emit light for detecting hydrogen gas from the surface side of the detection element on which the hydrogen gas detection layer is formed, it is necessary to dispose the light source and photodetector opposite the detection element, with an atmosphere to be measured containing hydrogen gas being present therebetween. Thus, the device configuration for detecting hydrogen gas to be detected is complex, and improvements in simplicity are also sought.

A hydrogen gas sensor that detects hydrogen gas has been described above, but the chemical sensor is not limited to being a hydrogen gas sensor that detects hydrogen gas, and includes such chemical sensors as ion sensors typified by pH (hydrogen ion index) sensors; gas sensors that detect oxygen, carbon dioxide, chlorine, nitrogen oxides, or the like; and biosensors that detect biomolecules such as DNA (deoxyribonucleic acid) and enzymes. Simplification of the device configuration and improvement in detection performance are also sought for such ion sensors, gas sensors, and biosensors in order to detect pH; gases such as oxygen, carbon dioxide, chlorine, nitrogen oxide; DNA and enzymes; and the like in a simple and high accuracy manner.

An optical detection type chemical sensor of one embodiment of this specification has a light source, a detection element, and a photodetector, the detection element is constituted of a laminate that includes a chemical detection layer, an optical interference layer, and a half mirror layer that are formed on a transparent substrate, and any one of the chemical detection layer, the optical interference layer, and the half mirror layer contains a magnetic material. According to the optical detection type chemical sensor of one embodiment of this specification, when light emitted from the light source is applied to the detection element, the light is emitted from the light source to the detection element under the condition that the light enters the inside of the detection element from the rear surface of the transparent substrate on which the laminate is not formed and multiple reflection occurring in the laminate intensifies the magneto-optical effect. The optical detection type chemical sensor is characterized by measuring the subject to be detected by measuring, using the photodetector, the change in optical properties of the chemical detection layer resulting from a reaction with the subject to be detected as a magneto-optical signal that indicates a change in the reflected light from the laminate. In this case, the magneto-optical signal is not affected by the intensity of the emitted light, and thus, even if the output from the light source were to fluctuate, stable detection of the subject is possible. Also, the thickness of the chemical detection layer can be set to a few dozen nm or greater, for example, and thus, it is possible to reduce the effect in the detection signal from fluctuation in the surface state of the chemical detection layer, and it is possible to detect the subject in a more stable manner. Additionally, the light source, the detection element, and the photodetector constituting the optical detection type chemical sensor of an embodiment of this specification can be arranged on only one side of an atmosphere to be measured that contains the subject to be detected, and thus, it is possible to simplify the device configuration. As described above, a highly reliable optical detection type chemical sensor that can stably detect a subject to be detected with a simple device configuration can be provided.

Also, the optical detection type chemical sensor of an embodiment of this specification can have a configuration by which a magnetic field application mechanism is added to the light source, the detection element, and the photodetector. The detection element is constituted of a laminate that includes a chemical detection layer, an optical interference layer, and a half mirror layer that are formed on a transparent substrate, and any one of the chemical detection layer, the optical interference layer, and the half mirror layer contains a magnetic material. When light emitted from the light source is applied to the detection element, the light is emitted from the light source to the detection element under the condition that the light enters the inside of the detection element from the rear surface of the transparent substrate on which the laminate is not formed and multiple reflection occurring in the laminate intensifies the magneto-optical effect. The optical detection type chemical sensor is characterized in that, by controlling the magnetization of a magnetic material contained in the laminate using the magnetic field application mechanism, the magneto-optical signal indicating a change in the light reflected by the laminate is modulated. According to this configuration, it is possible to provide an optical detection type chemical sensor with a higher detection accuracy by which the effect of noise in the detection signal can be reduced.

Additionally, it is preferable that the magnetic material contained in the laminate be a perpendicularly magnetized material, and in particular, it is preferable that the magnetic material be a CoPT (cobalt and platinum) alloy. According to this configuration, the magneto-optical signal resulting from multiple reflection occurring in the laminate can be greatly intensified, and thus, the effect of being able to detect hydrogen gas at a high sensitivity is exhibited.

Additionally, it is preferable that a configuration be adopted in which an anti-reflection film, a prism, or the like is used on the rear surface of the transparent substrate that is irradiated with light from the light source to reduce the amount of light reflected by the transparent substrate. According to this configuration, it is possible to increase the proportion of the detection signal within the measurement light, thereby exhibiting the effect of being able to detect the subject to be detected at a higher sensitivity.

Additionally, if the optical detection type chemical sensor according to an embodiment of this specification is a hydrogen gas sensor that detects hydrogen gas, then it is preferable that the chemical detection layer of the detection element be a thin film having, as the primary component, Pd (palladium), which undergoes a change in optical properties at room temperature upon contact with hydrogen gas, and in particular, it is preferable that the chemical detection layer have a thickness of 20 nm or greater. According to this configuration, it is possible to detect hydrogen gas at room temperature without the need for a heating mechanism, thereby exhibiting the effect of being able to detect hydrogen gas in a safe and stable manner with low energy consumption.

What is claimed is:

1. An optical detection type chemical sensor, comprising:
   a light source;
   a detection element; and
   a photodetector,
   wherein the detection element is constituted of a laminate in which a multilayer film including a chemical detection layer, an optical interference layer, and a half mirror layer is formed on a transparent substrate,
   wherein at least one of the chemical detection layer, the optical interference layer, and the half mirror layer constituting the laminate includes a magnetic material,
   wherein light emitted from the light source is applied to the detection element under the condition that the light enters inside of the detection element from a rear surface of the transparent substrate on which the laminate is not formed and multiple reflection occurring in the laminate intensifies the magneto-optical effect, and
   wherein a subject to be detected is detected by using the photodetector to detect a magneto-optical signal indicating a change in reflected light from the laminate resulting from a change in an optical property resulting from a reaction in the chemical detection layer.

2. The optical detection type chemical sensor according to claim 1,
   wherein the magneto-optical signal indicates a change in polarizing angle, a change in intensity, or a change in ellipticity of the reflected light from the laminate.

3. The optical detection type chemical sensor according to claim 1,
   wherein the chemical detection layer of the laminate is a hydrogen gas detection layer that undergoes a change in an optical property as a result of contact with hydrogen gas.

4. The optical detection type chemical sensor according to claim 1,
   wherein the chemical detection layer of the laminate is a thin film having palladium as a primary component.

5. The optical detection type chemical sensor according to claim 1,
   wherein a thickness of the chemical detection layer of the laminate is 20 nm or greater.

6. The optical detection type chemical sensor according to claim 1,
   wherein the magnetic material contained in the laminate is a perpendicularly magnetized film in which an axis of easy magnetization thereof is in a film surface normal direction.

7. The optical detection type chemical sensor according to claim 6,
   wherein the magnetic material contained in the laminate is an alloy of cobalt and platinum.

8. The optical detection type chemical sensor according to claim 1,
   wherein the transparent substrate has an antireflection film formed on the rear surface thereof which is irradiated with light from the light source, or the transparent substrate is optically coupled to the prism.

9. The optical detection type chemical sensor according to claim 1,
   wherein the photodetector is constituted of a light measurement device that measures an intensity of light passing through a polarizer.

10. The optical detection type chemical sensor according to claim 1,
    wherein the photodetector is constituted of two light measurement devices that measure an intensity of each of two beams of light formed by being split by a polarizing optical splitter.

11. The optical detection type chemical sensor according to claim 1, further comprising:
    a magnetic field application mechanism that controls magnetization of the laminate.

* * * * *